United States Patent [19]

Dempsey, Jr.

[11] Patent Number: 4,557,275
[45] Date of Patent: Dec. 10, 1985

[54] BIOFEEDBACK SYSTEM

[76] Inventor: Levi T. Dempsey, Jr., 6701 Seat Pleasant Dr., Seat Pleasant, Md. 20743

[21] Appl. No.: 496,465

[22] Filed: May 20, 1983

[51] Int. Cl.[4] .......................... G08B 21/00; A61B 5/04
[52] U.S. Cl. ..................................... 128/782; 128/573
[58] Field of Search ................ 128/733, 782; 340/573, 340/703

[56] References Cited

U.S. PATENT DOCUMENTS

| | | | |
|---|---|---|---|
| 3,208,062 | 9/1965 | Gregory . | |
| 3,588,858 | 6/1971 | Demuth | 340/573 X |
| 3,798,631 | 3/1974 | Langford | 340/573 X |
| 3,895,366 | 7/1975 | Morris | 340/573 X |
| 3,942,516 | 3/1976 | Glynn et al. | 128/733 X |
| 4,408,192 | 10/1983 | Ward et al. | 128/782 X |

FOREIGN PATENT DOCUMENTS 2491991 4/1980 Fed. Rep. of Germany ...... 128/733

OTHER PUBLICATIONS

Armstrong et al., "Use of Ramp ... Muscular Control", Med. & Biol. Eng. & Comput., Mar. 1979, pp. 268–270.

Primary Examiner—Edward M. Coven
Attorney, Agent, or Firm—Leonard Bloom

[57] ABSTRACT

A biofeedback system including a plurality of switches, for example mercury switches, which can be positioned on a patient's body and operatively arranged to respond to changes in orientation or position of a body member such as, for example, a patient's hand, wrist and forearm. Circuitry is arranged to respond to the closing of respective ones of the switches and develop specific, distinct biofeedback signals, for example, individual audible and visual signals for respective switch closings. An additional plurality of switches of the same construction can be placed on a therapist and be operatively arranged and connected to demonstrate the movements and illustrate the nature of the feedback signals.

14 Claims, 12 Drawing Figures

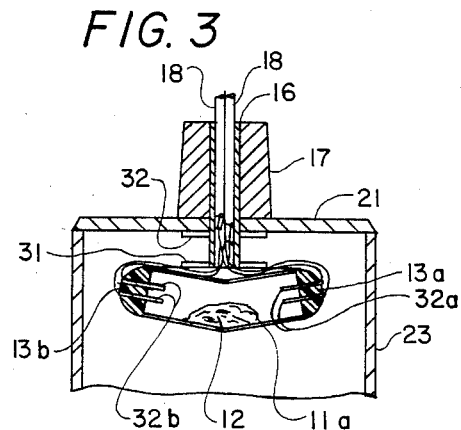
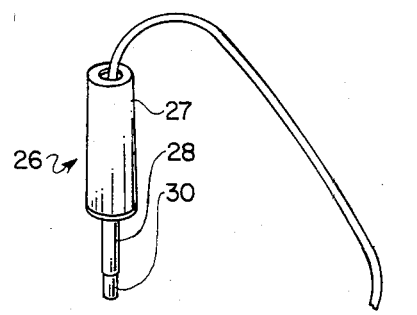
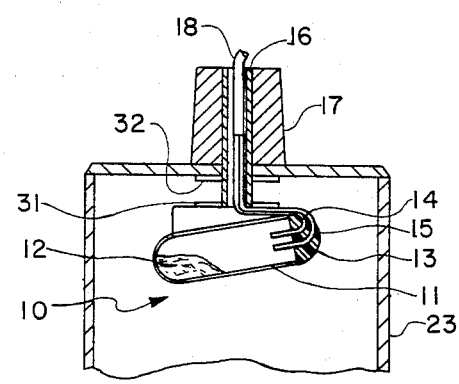
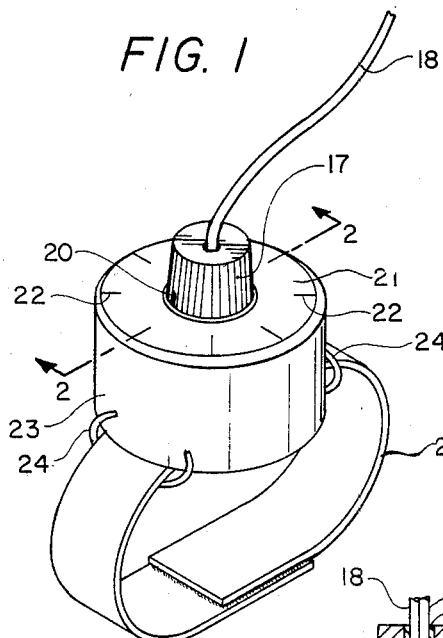
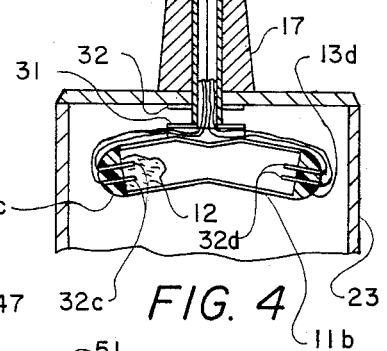
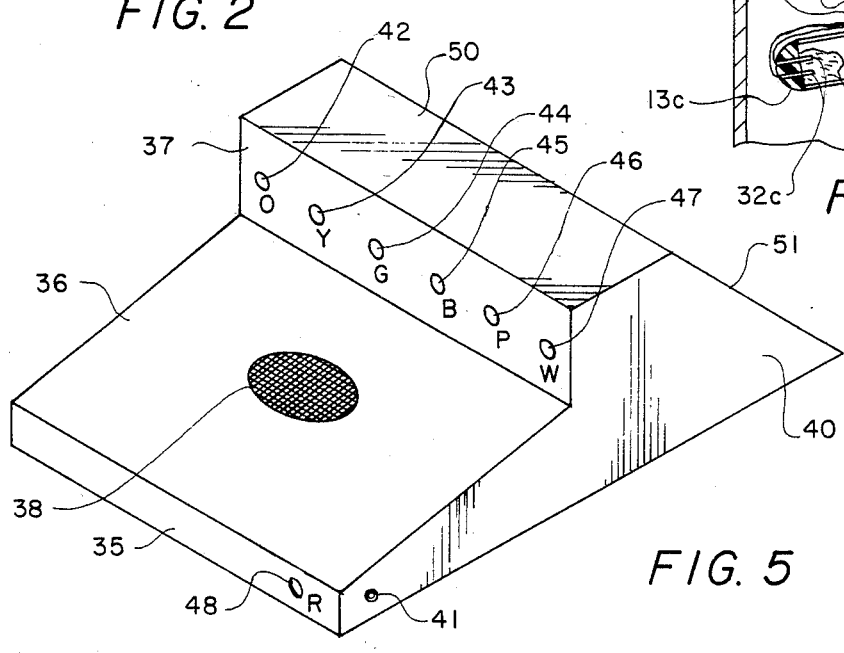

BIOFEEDBACK SYSTEM

BACKGROUND OF THE INVENTION

This invention relates to a biofeedback system particularly useful in rehabilitation therapy. The invention relates, more particularly, to a biofeedback system suitable in the treatment of motor neuron lesions particularly in the retraining of muscles and reeducating patients who have suffered strokes or have been subjected to neurologic trauma.

A recent summary of biofeedback techniques appears in an article of Basmajian, John V., MD, "Biofeedback in Rehabilitation: A Review of Principles and Practices", *Arch. of Physical Medicine and Rehabilitation,* Volume 62, No. 10, pages 469–475, October 1981. The article describes known techniques of using electronic equipment to reveal to patients and therapists certain physiologic events and to teach patients to control events by manipulating the event related signals, which usually are visual and/or acoustic. Biofeedback has gained recognition especially in the treatment of upper motor neuron lesions, particularly in retraining muscles and inducing relaxation of muscles of stroke patients and the like. The broad concepts of using electrogoniometers, pressure-sensitive and position-sensing devices as transducers is recognized.

Another summary, S.J. Middaugh, "Electromyographic Feedback: Effects on Voluntary Muscle Contractions in Normal Subjects", *Arch. of Physical Medicine and Rehabilitation,* Volume 63, No. 6, pages 254–259, June 1982, recognizes the possibility of using a voltage controlled oscillator producing a tone which is related to electromyographic feedback as an improvement in simple trial-and-error-learning.

Among body and limb position sensing devices are usually switches such as disclosed in the U.S. Pat. No. 3,614,763 to Yannuzzi entitled "Prone Position Alarm", issued Oct. 19, 1971. The mercury switch is positioned within a housing which also includes an audio oscillator which sounds an alarm, the housing being operatively associated with a clip which may be placed on a user's belt. Another proposal for the use of a mercury switch in association with a limb position sensing device is known from the U.S. Pat. No. 3,885,576 to Symmes entitled "Wrist Band Including A Mercury Switch To Induce An Electric Shock", issued May 27, 1975.

Of more general interest, are the teachings in the U.S. Pat. Nos. 4,191,949 and 3,208,062 to Myers and Gregory, respectively, these patents disclosing respectively a position warning device, associated with an otherwise conventional belt, and a signal device for alerting a user to the nodding of his head.

OBJECTS AND SUMMARY OF THE INVENTION

An object of the present invention is to provide a biofeedback system which is especially useful in rehabilitative therapy and is simple, versatile and inexpensive.

Another object of the present invention is to provide a biofeedback system which allows a therapist to intervene in the system in a demonstrative way, while engaged in rehabilitative therapy and the like.

An additional object of the present invention is to provide a biofeedback system which allows a patient to effect a series of actions and receive specific, distinct biofeedback signals for each respective action, and to repeat the series of actions.

The foregoing objects, as well as others which are to become clear from the text below, are achieved in accordance with the present invention by providing a biofeedback system which includes a plurality of switches, for example mercury switches, which can be positioned on a patient's body and operatively arranged to respond to changes in orientation or position of a body member such as, for example, a patient's hand, wrist and forearm. Circuitry is arranged to respond to the closing of respective ones of the switches and develop specific, distinct biofeedback signals, for example individual audible and visual signals for respective switch closings.

BRIEF DESCRIPTION OF THE DRAWINGS

FIG. 1 is a pictorial drawing of an exemplary sensing device which can be attached to a patient and incorporated into a biofeedback system according to the present invention.

FIG. 2 is a cross sectional view of a portion of the sensing device of FIG. 1, the section being taken along section line 2—2, and showing the position of a mercury switch within the housing portion of the sensing device.

FIG. 3 is a cross sectional view similar to that of FIG. 2, showing a modified version of the mercury switch arrangement of FIG. 2 in which four contacts rather than two are utilized and which can be incorporated in the biofeedback system of the present invention.

FIG. 4 is an additional modified mercury switch arrangement similar to that of FIG. 3 in which two pair of contacts are provided, and which may be used in the biofeedback system according to the present invention.

FIG. 5 is a pictorial view of a housing within which the circuit components of the present invention, other than those contained in the sensing devices, may be positioned, signal lights and a loud speaker grille being visible.

BRIEF DESCRIPTION OF THE PREFERRED EMBODIMENT

Figure 6:
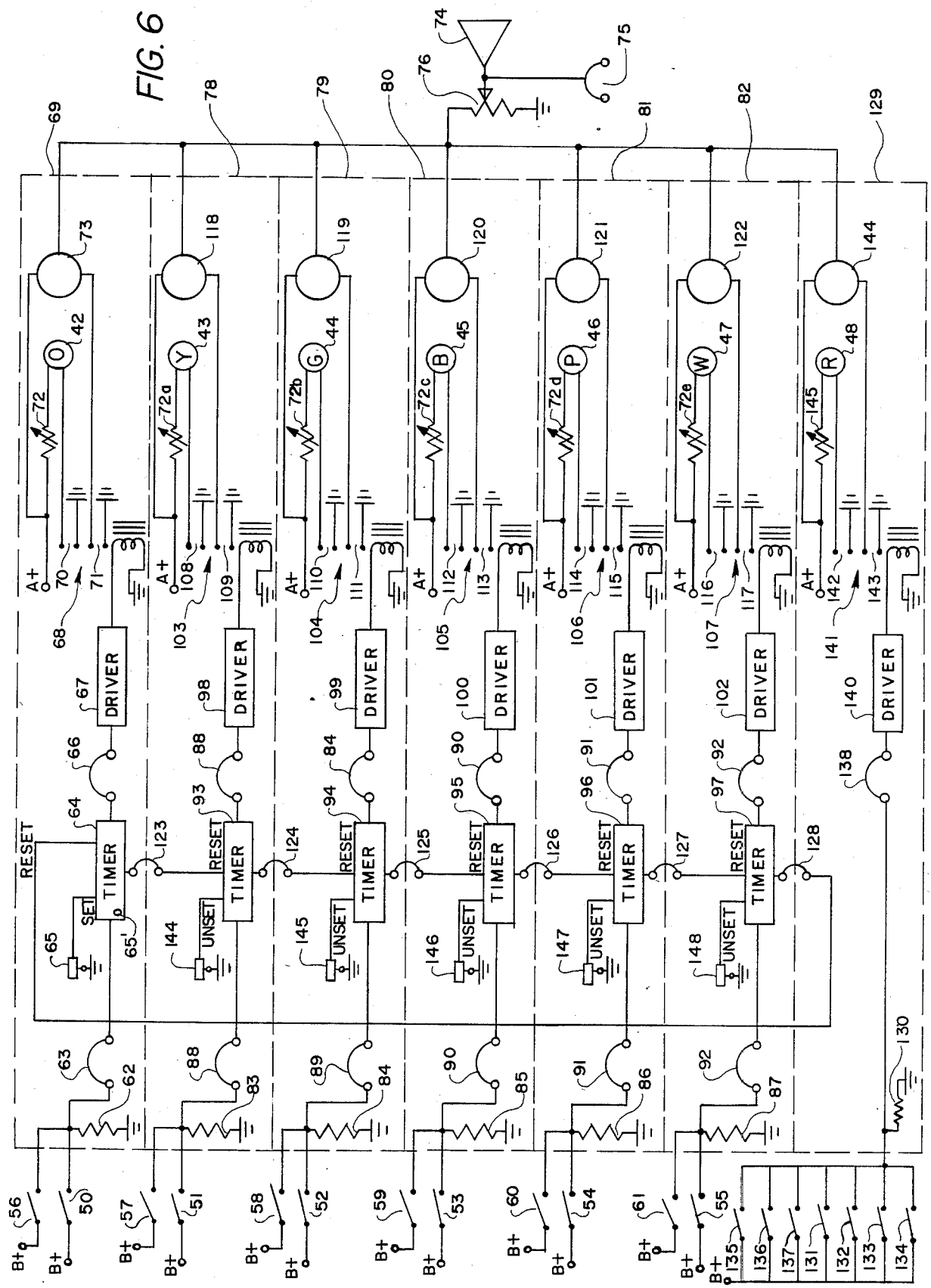
FIG. 6 is a schematic, block diagram illustrating an exemplary embodiment of a signal processing circuit which constitutes a major portion of the biofeedback system according to the present invention.

As shown in FIG. 2 a conventional mercury switch referred generally by the numeral 10 which may be utilized in practicing the present invention includes a substantially cylindrical glass member 11 having its lowermore end closed by an integral extension of the glass member 11, a pool of mercury 12 being shown thereat. The other end of the cylindrical glass member 11 is closed by a suitable insulating plug 13, which may be made of plastic or the like. A pair of conductive leads 14, 15 extend through the insulating plug 13 into the interior of the glass member 11, the free ends of these conductive leads 14, 15 constituting an open circuit which would be closed were the pool of mercury 12 in contact therewith.

The conductive leads 14, 15 are suitably covered with insulation, are spaced apart and are partially encapsulated within the insulating plug 13. The insulation, which may enable, extends over those portions of the leads 14, 15 which extend to the outside of the switch 10. The leads 14, 15 are positioned on the outside of the cylindrical glass member 11 and thereafter are bent upwardly extending through a hollow-cylindrical metallic sleeve 16 which is fixed centrally and extends through a knurled knob 17. A protective insulation sleeve 18 extends over the insulated leads 14,15.

Referring to FIGS. 1 and 2, the knurled knob 17 is provided on its outer surface with a visible vertical mark 20 and is movably positioned over a circular member 21 having indicia 22, for example degree marks, at fixed intervals on a portion thereof near its periphery. The circular member 21 is fixedly positioned as a closure member over the top of a cylindrical member 23, which is closed at its bottom and is provided with a pair of ring members 24 which extend from the near the bottom of the cylindrical member 23 and through which a flexible band 25 extends. The flexible band 25 is provided at its free ends with velcro so that the free ends may be brought into contact and fixedly hold itself fast. It is to be appreciated that other conventional techniques or members can be provided for closing the flexible member 25 so as to position the sensing device shown in FIG. 1 about the wrist, arm, hand or other body member of a therapist or patient, as the cases may be. The flexible protective insulation sleeve 18 extends upwardly from the knurled knob 17 with the insulated conductive leads 14, 15 inside the same, terminating within a plug 26 having its connections within a cylindrical housing 27 which has extending therefrom conventional male contacts 28, 30 insulated from one another and which are in conductive contact with the conductive leads 14, 15 as they terminate within the housing 27.

As particularly visible in FIG. 2, the mercury switch 10 is carried beneath inner surface of the circular member 21 by a circular flange 31 which extends outwardly from the cylindrical member 16. A suitable washer 32 or the like is positioned about the cylindrical member 16 immediately below the inner surface of the circular member 21 and spaced from the flange 31. A spring or the like (not shown for the sake of simplicity), is positioned between the washer 32 and the circular flange 31 so as to hold the sleeve 16 and the mercury switch 10 in position so that the mercury switch 10, can be rotated by manually manipulating the knurled knob 17, the mark 20 on the outside of the knurled knob 17 indicating the relative position of the lower-more end of the cylindrical member 11 at any given time.

Two variants of the mercury switch are illustrated in FIGS. 3 and 4, respectively, as being positioned within respective cylindrical member 23, which correspond to the member 23 shown in FIG. 2 corresponding parts of that portion of the respective sensing devices of FIGS. 3 and 4 are provided with the same references numerals used in FIGS. 1 and 2. In FIG. 3 two pair of contacts 32a, 33b are provided in respective ends of a V-bent cylindrical member 11a, an insluating plug 13a and 13b being provided in the respective ends of the member 11a. In FIG. 4 two pair of contacts 32c and 32d are provided in respective ends of an inverted V-bent cylindrical member 11b. In this case insulating plugs 13a and 13d are provided in respective ends of the member 11b.

The signal of processing circuitry of the present invention is preferably housed within plain-looking console, a suitable configuration for such a console being illustrated pictorially in FIG. 5. As shown in FIG. 5, the front of the console includes a vertical, rectangular panel 35 a backwardly slanted panel 36, and a second, relatively narrow vertically extending panel 37. Centrally located on the sloping panel 36 is a grill work 38 behind which a loudspeaker is positioned. The console is provided with side panels, the right-side panel 40 being visible in FIG. 5. Out of sight of the patient, so as not to distract the patient is a female plug 41 into which a male plug associated with a pair of earphones could be inserted were one to decide not to utilize the loudspeaker behind the grill work 38 as the audio biofeedback signaling device, electing instead to use the earphones. Visual biofeedback devices are constituted by a plurality of lamps positioned longitudinally behind the rectangular panel 37 and viewable through apertures therein, the lamps constituting the distinctive, different colored light sources illustrated as lamps 42–47 which are respectively associated with filters to provide the differing colors. As illustrated the lamps in the order named provide distinct color outputs, 42–47 these colors could be for example, orange, yellow, green, blue, purple and white as indicated by the letters O, Y, G, B, P, and W, respectively, beneath the lamps on the panel 37. It is preferable, nevertheless, that the letters do not appear beneath the respective light sources so as not to unnecessarily detract a patient from the visual stimuli from the distinctive, color light sources 42–47. A seventh viewable color source 48 is visible to a patient, this seventh light source being constituted by a further lamp with filter behind the panel 35 and indicated as being a red source by the letter R appearing on the panel 35. Here again, it is preferable that the letter R not appear on the panel so as to be viewable by the patient and thus serve as a possible distraction to the patient.

The console includes a longitudinal top panel 50 and a downwardly sloping back panel, as can be discerned by viewing an edge 51 thereof where the back panel meets the side panel 40.

Signal processing circuitry is illustrated in FIG. 6 suitable for practicing the present invention. As connected in FIG. 6, the circuitry is arranged so as to provide audible and visual biofeedback signals to a patient in response to six distinct motions of the patient, who may for example, be a stroke victim undergoing retraining in the use of his forearm, wrist and hand, and who may have some right-left confusion. For purposes of illustration, the body movements could be constituted of (1) flexing of a forearm, (2) extending of a forearm; (3) grasping of a hand, (4) release of a hand, (5) supination of a wrist, and (6) pronation of a wrist, respectively.

As illustrated in FIG. 6, six mercury switches which are to be strapped to a patient are shown schematically, respectively as switches 50–55, which would during treatment be removeably fixed to the patient by strapping sensing devices, such as shown in FIGS. 1–4 to the patient. As a practical matter one would select one or the other of the switches shown in FIGS. 2–4 for the switches to be attached to a patient. The FIG. 2 arrangement being especially suitable for the forearm, the FIG. 3 arrangement for the wrist and the FIG. 4 arrangement for the hand or fist.

As a possible further feature of the invention, in a preferred form, the circuitry of FIG. 6 is provided with six additional switches 56–61 which would be removably fixed to the therapist in the same fashion and at corresponding locations as those associated with the patient so the therapist can demonstrate the desired movements resulting in the same visual and audible biofeedback signals which the patient would produce were patient properly to move his arm, for example, in the fashion and in the sequence which the therapist wishes the patient to do.

Before turning to the details of the over-all circuitry shown in FIG. 6, one channel thereof will first be described. The mercury switch 50 is positioned electrically between a voltage source indicated as B+, and a point of reference voltage, illustrated as being ground, the switch 50 being connected between B+ and ground via a resistor 62. Also connected between B+ and ground, via the same resistor 62 is the mercury switch 56 which is to be strapped to the therapist. The ungrounded end of the resistor 62 is connected, via a jumper 63 to the start terminal of a conventional electric or electronic timer 64, which also is provided with a resetting input and a manually operable set input, illustrated diagrammatically as a push button 65 which resets the timer 64 by grounding a point thereof. The timer 64 is also provided with a push button switch 65' which when depressed places the timer 64 in an ready condition, awaiting a set or resetting input signal. The timer 64 has two outputs, one being constituted by a terminal connected by a jumper 66 to the input of a driver 67, which in turn has its output connected in energizing relationship to the solenoid of a relay 68 which includes two pairs of contacts 70, 71 which are closed whenever the relay 68 is energized. As illustrated, a voltage source indicated as A+ is connected, via a variable resistor 72, to one side of the orange-light source constituted lamp 42, the other side of the lamp 42 being connectable to ground via the pair of contacts 70, upon energization of the relay 68. The second pair of contacts 71 of the relay 68 are connected in series with a tone generator 73 to the A+ source. Accordingly, whenever the relay 68 is energized, the pair of contacts 70 and the pair of contacts 71 close, causing respectively the orange-light emitting lamp 42 and the tone generator 73 to be energized. The variable resistor 72 can be manipulated by the therapist or the patient to provide for either dim or bright lighting of the orange-light emitting lamp 42, thus providing different intensities for the visual feedback signal which it provides. The tone generator 73 has an output which is preferably constituted by a particular musical tone or other pleasant sound is connected so as to energize a speaker 74 or a pair of earphones 75. As illustrated the output of the tone generator 73 is fed to the speaker 74 and/or the earphones 75 via a volume control potentiometer 76 so that the volume of the audible biofeedback signal can be varied, as it is adjusted by the therapist or the patient.

The timer 64 also is provided with a second output, which, as is to be explained below, is used to set the next timer in a series of timers, respective ones of the timers being associated with respected motions to be undertaken by the patient.

As indicated above, the six channels in the illustrated embodiment are of substantially identical construction, the second through six channels being shown respectively within dashed lines blocks 78–82, respectively. Each of the channels 78–82 include respective resistors 83–87 arranged like the resistor 62 with respect to the respective mercury switches is 51–55, which are to be associated with the patient, and mercury switches 57–61, which are to be associated if desired, with the therapist. The channels 78–82 as connected include respective jumpers 88–92 and 88'–92', respective timers 93–97 as well as respective drivers 98–102 and respective relays 103–107. The respective relays 103–107 include respective pairs of contacts 108, 109 and 110, 111 and 112, 113, and 114, 115 and 116, 117. The even numbered ones of these contacts are operatively connected to the A+ voltage source, via the adjustable resistors 72a–72e so as to energize respectively the distinct light emitting lamps 43–47 when the respective relays 103–107 are energized. It is to be understood, however, that each of the lamps 43–47 could be connected to the A+ terminal via the variable resistor 72, which also connects lamps 73 to the A+ terminal were all lamps to be dimmed at the same time and to the same extent. Similarly, the odd-numbered ones of the pairs of contacts relatively connected to the A+ voltage source via respective musical tone generators 118–122 which produce respectively distinct, preferably musical tones or distinct pleasant sounds which one can hear from the speaker 74 or earphones 75.

Respective signal channels 69 and 78–82 are intercoupled by connecting the reset input of the respective timers 64 and 93–97 to the setting output of the respective timers 97, and 93–96, these interconnections being shown and being provided via respective jumpers 128 and 123–127.

The signal processing system of FIG. 6 desirably includes additionally a seventh channel 129 which electrically is somewhat less complex than the channels 69 and 78–82. The seventh channel includes a resistor 130 which has one end grounded and the other band connected to the voltage source B+ via six microstitches illustrated as switches 130–137. The switches 131–137 are mercury switches which are, for example, removably fixed to the other arm of a patient at points corresponding to the placement of the microswitches 50–55. The purpose of the mercury switchees 131–137 is to provide, when they are respectively closed, an error-signal constituted by the appearance of a voltage across the resistor 130 which is fed, via a jumper 138 to a driver 140 which in turn upon receipt of an input signal energizes the relay 141 closing two pairs of contacts 142, 143, respectively which in turn upon receipt of an inpupt signal energizes the relay 141 closing two pairs of contacts 142, 143, respectively which in turn energize the red light lamp 38 and the tone generator 144 which, unlike the tone generators 73 and 118–122 produces a preferably non-musical sound which provides a special biofeedback to the patient which indicates to him that he has moved the wrong arm, for example. Dimming for the lamp 48 is provided by the variable resistor 145.

Turning briefly to FIGS. 8A–8E, and with further reference to FIG. 6, a brief discussion of the operational sequence is to be considered.

Once the patient and/or therapist has the six mercury switches 50–55 or 56–61, as the cases may be, positioned on his arm, wrist and hand as illustrated, the circuit of FIG. 6 is made ready by setting the first timer 64 in enabled condition by pressing the push button switch 65. It is to be assumed that all of the other timers 93–97 are not yet set, each having been placed in a ready, that is unset, condition by, for example, depressing the respective push buttons 144 to 148 or having run down as a result of previous use without having been reset.

Figure 8A:
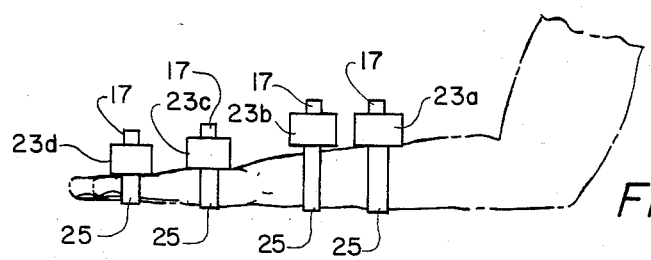
FIG. 8A–8E are respective pictorial illustrations of a patient's right arm with a number of sensing devices positioned and which are to aid one in understanding the operation of the biofeedback system according to the present invention.
Figure 8B:
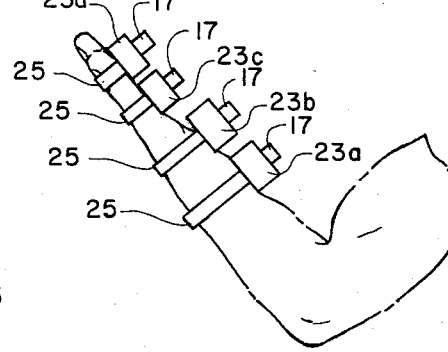

The patient then undertakes to move his arm, fist and wrist in a predetermined instructed sequence. For example, he first flexes his forearm moving it from the position as shown in FIG. 8A to that shown in FIG. 8B, this motion closes the mercury switch 50 which is within the cylindrical member 23a and starts the timer 64 running for a predetermined length of time, for example, two or three seconds. The output from the timer 64 is fed to the driver 67 which drives the relay 68, causing the pair of contacts 70 and the pair of contacts 71 to close thereby energizing the orange light emitting lamp 42 and the tone generator 73 which are respectively seen and heard by the patient. At the conclusion of the two or three second period of audible and visible feedback, the timer 64 emits a second output signal, which serves to reset the timer 93, making it ready to accept a start signal. The patient then returns his forearm to the position shown in FIG. 8C which closes the mercury switch 51 within the cylindrical member 23b, causing the timer 93, the driver 98 and the relay 103 to respond in the same fashion as just described above in conjunction with the first movement of the patient's forearm. In this case, the pairs of contacts 108, 109 close effecting the energization of the yellow light producing lamp 43 and the tone generator 118. Here again, the same sequence of events occur, different and distinctive light and audible signals are provided to the patient as biofeedback for a given period of time at the conclusion of which the timer 93 produces a output signal, via the jumper 124, to the timer 94 enabling it and making it ready to receive a start signal. Next the patient makes a fist (not illustrated), sometimes called a grasping action, as instructed by the therapist closing the mercury switch 52 which is within the cylindrical member 23c, causing the third channel 79 to operate much in the same fashion as the foregoing channels providing third audible and visual feedback signals to be produced by the tone generator 119 and the green lamp 44.

Figure 8E:
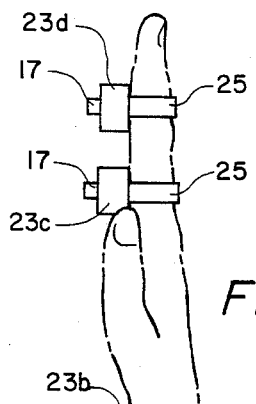
Figure 8D:
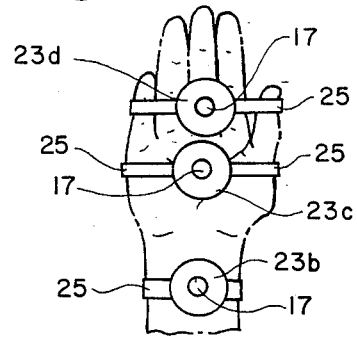
Figure 8C:
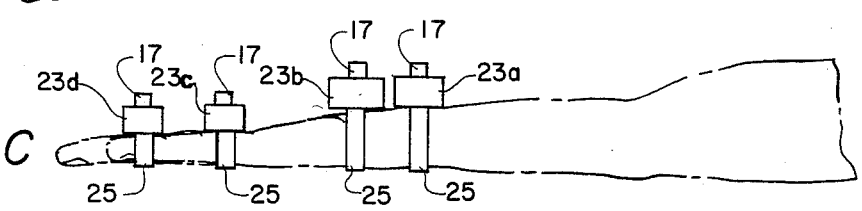

Similarly, the patient then releases his fist, receives a fourth biofeedback stimulation by the energization of the blue light emitting lamp 45 and the tone generator 120., as a result of closing mercury switch 53 Thereafter, as the tone and light signals disappear and the subsequent motions are made by the patient he releases his fist so that his arm, wrist and hand are in the position as shown in FIG. 8A and subsequently performs supination and pronation movements, achieving the hand positions as illustrated respectively in FIGS. 8D and 8E; each of these motions causes respective tone generators 121, 122 and respective purple and white lamps 46, 47, via the channels 81, 82, to respond providing, distinctive visual and audible responses. Upon the ending of the signals produced as a result of the energization of the relay 107, part of the last channel 82, which was energized upon pronation of the patient's wrist, the final timer 97 produces its reset signal which is coupled, via the jumper 128 to the set input of the timer 64 and the whole sequence of events can then again take place. This can be done over and over again until the patient relearns. During this time, the intensity of the visual and audible biofeedback signals can be reduced by manipulation respectively of the variable resistors 72, 72a, 72b and the volume control potentiometer 76 by the therapist as an aid in reducing the dependence of the patient on the biofeedback signals, making him rely to a higher degree on his own mental processes.

As illustrated, because each of the timers 64 and 93-97 in firstly "run down" or unset by momentarily depressing push buttons 144-148 and the system made ready by depressing push button 65 to set the system on one channel and the closing of one mercury switch at any time effects operation, whether any or all of the other switches are open or closed at any time is not important because the timers in the other channels will not start.

Were the patient to unexpectedly move the wrong arm, to which the six additional mercury switches 131-137 have been strapped in the fashion intended, a voltage would be produced across the resistor 130 and coupled via the jumper 138 to the input of the driver 142, causing the relay 141 to be energized. The energization of the relay 141 close the pairs of contacts 142, 143 causing the red light light source lamp 48 to become energized and an unpleasant tone to be produced by the tone generator 144 signaling both to the therapist and the patient that he has made a wrong movement.

Were the therapist to have fixedly positioned corresponding mercury switches to his own forearm, wrist and hand, these mercury switches being represented by the switches 56-61, he could initially instruct a patient by example or intervene in the biofeedback process to illustrate the movements he wishes the patient to make.

Figure 7:
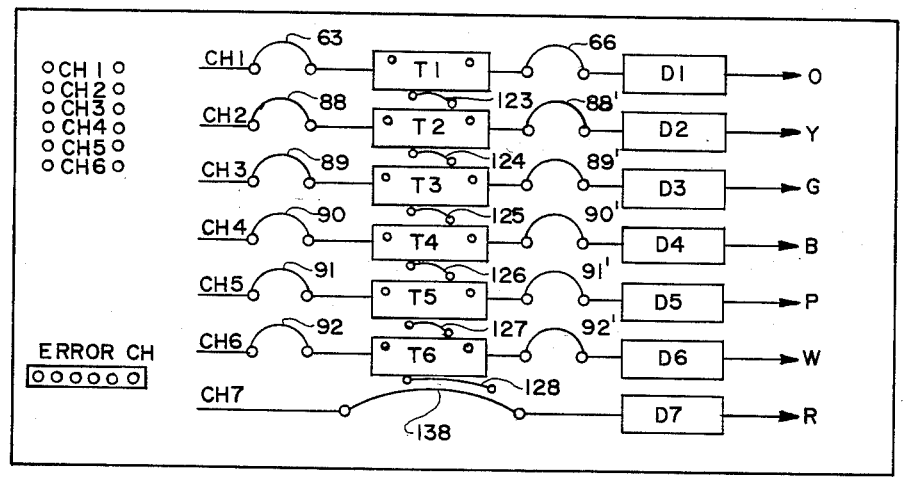
FIG. 7 is a simplified diagram of the back of the housing shown in FIG. 5, switch-board apertures, into which male plugs may be placed, being visible as well as exemplary connections between some of the apertures of suitable plugs in the form of jumpers also shown in FIG. 6.

By way of example, the back of the console shown in FIG. 5 may advantageously appear as shown in FIG. 7, the jumpers 63, 66, 88-92, 88'-92' and 138, and 123-128, shown schematically in FIG. 6, can be patch cords connecting female jacks as shown in FIG. 7. The patient (P) and therapist (T) input female jacks can be seen in the upper left-hand portion of FIG. 7 associated with channels 1-6 (CH1-CH6), the six error input female jacks being shown in the lower-left portion of FIG. 7. Male jacks, such as jack 26 (FIG. 1), are insertible in the above mentioned female jacks. Respective timers for respective channels CH1-CH6 are diagramatically shown as T1-T6, the drivers for the respective orange (O), yellow (Y), green (G), blue (B), purple (P), white (W) and red (R) lamps being shown as D1-D7.

This is to be appreciated that the foregoing description and the accompanying drawings relate to illustrative preferred embodiment. It is to be appreciated that numerous other embodiments in varience are possible within the spirit and scope of the invention, it scope being defined by the appended claims.

What is claimed is:

1. A biofeedback system comprising a plurality of sensing means which are to be removeably fixed to a patient for producing a corresponding plurality of respective signals in the response to change in position of portions of the body of the patient with respect to a given plane outside of the body of the patient and signal processing means coupled to said plurality of sensing means and responsive to the respective signals therefrom for developing different, sequential, distinctive signals which can be sensed by the patient and result from respective sequentially positioning of portions of the body of patient.

2. A biofeedback system comprising a plurality of force-of-gravity responsive sensing means which are to be removeably fixed to a patient for producing a corresponding plurality of respective signals in response to change in position of portions of the body of the patient with respect to a given plane outside of the body of the patient and signal processing means coupled to said plurality of sensing means and responsive to signals therefrom for developing signals which can be sensed by the patient, and wherein said signal processing means includes circuit means for producing different, sequential, distinctive signals which can be sensed by patient and result from respective sequential positioning of portions of the body of the patient.

3. A biofeedback system according to claim 2, wherein said circuit means comprises means for producing a sequence of different distinctive visible signals in response to respective sequential positioning of portions of the body of the patient.

4. A biofeedback system according to claim 3, wherein said means for producing a sequence of different distinctive visual signals includes a plurality of differently colored sources of light.

5. A biofeedback system according to claim 2, wherein said circuit means comprises means for producing a sequence of different distinctive audible signals in response to respective sequential positioning of portions of the body of the patient.

6. A biofeedback system according to claim 5, wherein said means for producing a sequence of different distinctive audible signals includes a plurality of generators each producing a distinctive different tone or musical note.

7. A biofeedback system according to claim 2, wherein said circuit means comprises means for producing a sequence of different distinctive visible signals in response to respective sequential positioning of portions of the body of the patient and means for producing a different distinctive audible signal in response to respective sequential positioning of portions of the body of the patient.

8. A biofeedback system according to claim 7, wherein said means for producing a sequence of different distinctive visual signals includes a plurality of differently colored sources of lights and said means for producing a sequence of different distinctive audible isgnals includes a plurality of generators each producing a distinctive different tone or musical note.

9. A biofeedback system according to claim 1 or 2, including a further plurality of sensing means which are to be removably fixed to a therapist for producing a further corresponding plurality of signals in response to change in position of portions of the body of the therapist, said signal processing means being coupled to said further plurality of sensing means and being responsive to signals therefrom for developing further sequential distinctive signals which can be sensed by the patient and result from perspective sequential positioning of portions of the body of the therapist.

10. A biofeedback system according to claims 1 or 2, including at least one additional sensing means which is to be removeably fixed to the patient, and additional signal processing means coupled to and responsive to signal from said at least one additional sensing means for providing at least one distinct signal in response to movement of said at least one additional sensing means.

11. A biofeedback system according to claim 10, wherein said additional signal processing means includes additional circuit means for producing at least one distinct audible signal in response to movement of said at least one additional sensing means.

12. A biofeedback system according to claim 10, wherein said additional signal processing means includes additional circuit means for producing at least one distinct visible signal in response to movement of said at least one additional sensing means.

13. A biofeedback system according to claim 10, wherein said additional signal processing means includes additional circuit means for producing at least one distinct visible signal and one distinct audible signal in response to movement of said at least one additional sensing means.

14. A biofeedback system according to claim 1 or 2, wherein said signal processing means are operatively arranged for respectively producing repetitive sequences of different distinctive siganls which can be sensed by the patient in response to repeditive respective sequential positions of portions of the body of the patient.

* * * * *